United States Patent [19]

Niznick

[11] Patent Number: 4,960,381

[45] Date of Patent: Oct. 2, 1990

[54] SCREW-TYPE DENTAL IMPLANT ANCHOR

[75] Inventor: Gerald A. Niznick, Encino, Calif.

[73] Assignee: Core-Vent Corporation, Encino, Calif.

[21] Appl. No.: 231,653

[22] Filed: Aug. 10, 1988

Related U.S. Application Data

[63] Continuation of Ser. No. 1,564, Jan. 8, 1987, abandoned.

[51] Int. Cl.⁵ ............................................. A61C 8/00
[52] U.S. Cl. ..................................... 433/174; 433/173
[58] Field of Search ............... 433/173, 174, 176, 221, 433/225; 623/16

[56] References Cited

U.S. PATENT DOCUMENTS

| | | | |
|---|---|---|---|
| 711,324 | 10/1902 | Lacy | 433/174 |
| 866,304 | 9/1907 | Roach | 433/177 |
| 2,112,007 | 3/1938 | Adams | 433/174 |
| 2,347,567 | 4/1944 | Kresse | 433/174 |
| 2,609,604 | 9/1952 | Sprague | 433/174 |
| 3,435,526 | 4/1969 | Brancato | 433/174 |
| 3,499,222 | 3/1970 | Linkow et al. | 433/174 |
| 3,732,621 | 5/1973 | Bostrom | 433/174 |
| 4,016,651 | 4/1977 | Kawahara et al. | 433/174 |
| 4,109,383 | 8/1978 | Reed et al. | 433/176 |
| 4,177,562 | 12/1979 | Miller et al. | 433/174 |
| 4,180,910 | 1/1980 | Straumann | 433/173 |
| 4,187,609 | 2/1980 | Edelman | 433/176 |
| 4,342,550 | 4/1982 | Reuther et al. | 433/174 |
| 4,359,318 | 11/1982 | Gittleman | 433/173 |
| 4,416,629 | 11/1983 | Mozsary et al. | 433/174 |
| 4,431,416 | 2/1984 | Niznick | 433/174 |
| 4,468,200 | 8/1984 | Munch | 433/174 |
| 4,488,875 | 12/1984 | Niznick | 433/173 |
| 4,552,532 | 11/1985 | Mozsary | 433/173 |
| 4,624,673 | 11/1986 | Meyer | 433/173 |
| 4,626,214 | 12/1986 | Artal | 433/174 |
| 4,645,453 | 2/1987 | Niznick | 433/173 |
| 4,661,066 | 4/1987 | Linkow et al. | 433/176 |
| 4,713,004 | 12/1987 | Linkow et al. | 433/174 |

FOREIGN PATENT DOCUMENTS

| | | | |
|---|---|---|---|
| 73177 | 8/1982 | European Pat. Off. | 433/173 |
| 3027138 | 12/1981 | Fed. Rep. of Germany | 433/174 |
| 42665 | 10/1976 | Japan | 433/174 |
| 83591 | 1/1977 | Japan | 433/173 |
| 1291470 | 10/1972 | United Kingdom | 433/173 |
| 1352188 | 5/1974 | United Kingdom | 433/174 |
| 1544784 | 4/1979 | United Kingdom | 433/173 |

OTHER PUBLICATIONS

The Journal of Prosthetic Dentistry vol. 50, No. 1, published by The C. V. Mosby Company, in Jul. 1983. Promotional Literature for Zest Anchor.

*Primary Examiner*—John J. Wilson

[57] ABSTRACT

A screw-type dental implant anchor includes an externally-threaded body portion having internal structure for engaging an insertion tool. The body portion can be joined to a top portion having an unthreaded exterior wall. This internal is inside a top portion or inside the body portion of the anchor. The top portion is open, preferably chamfered at its upper end, and in registration with an internally-threaded shaft inside the body portion of the anchor that extends from a plane just below the head portion downwardly a substantial distance inside the body portion. The distal end of the anchor includes a through hole extending from one side of the body portion to the other, and an opening at the bottom of the body portion extending upwardly inside the body portion a distance sufficient to permit bone and associated tissue to grow into and through these openings and to permit blood tissue to escape.

44 Claims, 2 Drawing Sheets

SCREW-TYPE DENTAL IMPLANT ANCHOR

This application is a continuation of application Ser. No. 001,564, filed Jan. 8, 1987, now abandoned.

This invention relates to a screw-type dental implant anchoring means comprising an externally-threaded, preferably self-tapping, body portion. The implant has internal means for engaging means for inserting the implant into an opening formed in bone tissue to receive the implant. This internal means is, preferably, a wrench-engaging surface. In preferred embodiments, the body portion is joined to a top portion having an unthreaded exterior wall. Preferably, the internal means for implant insertion is inside that top portion, but can alternatively be inside the body portion. The top or head portion is open, preferably chamfered at its upper end, and in registration with an internal, threaded shaft. This shaft is inside the body portion of the anchor, and extends from a plane just below the head portion downwardly a substantial distance inside the body portion of the anchor.

The distal end of the anchor preferably includes a through hole extending from one side of the body portion to the other. The distal end also includes an opening at the bottom of the body portion extending upwardly inside the body portion a distance sufficient to permit bone and associated tissue to grow into and through these openings, and to permit blood tissue to pass through, but preferably less than about one-third the length of the body portion itself.

Preferably, the head portion has a hex nut configuration on its inner wall surfaces for receiving a hex wrench, and has a cylindrically-shaped, smooth outer wall. Alternatively, the hex nut configuration can be within, and preferably at the base of the shaft inside the body portion. The internal hex nut configuration permits the insertion of the anchoring means in the jawbone of a subject without countersinking the upper surface of the bone where the head portion of the anchoring means lies when the anchoring means is properly inserted in the jaw. Preferably, the head portion has an outer circumference no greater than the circumference of the externally-threaded body portion that is joined to the head portion, thus obviating any need to enlarge the top of the opening in a bone to permit proper insertion of the anchoring means.

The head portion is preferably chamfered at its open, upper end. This chamfered surface permits frictional locking with any adaptor or other connecting means inserted into the opening, is of sufficient size and depth to afford lateral stability to any adaptor or other connecting means inserted into the opening in the head portion, and forms a smooth, easily cleaned margin with complementary connecting means inserted into the opening of the head portion.

The anchoring means is preferably made of commercially-pure titanium, and preferably has an outside thread diameter of not more than about 4 millimeters. The anchoring means preferably has a length in the range of about 5 to about 20 millimeters in preferred embodiments.

This invention can better be understood by reference to the drawings, in which.

Figure 1:
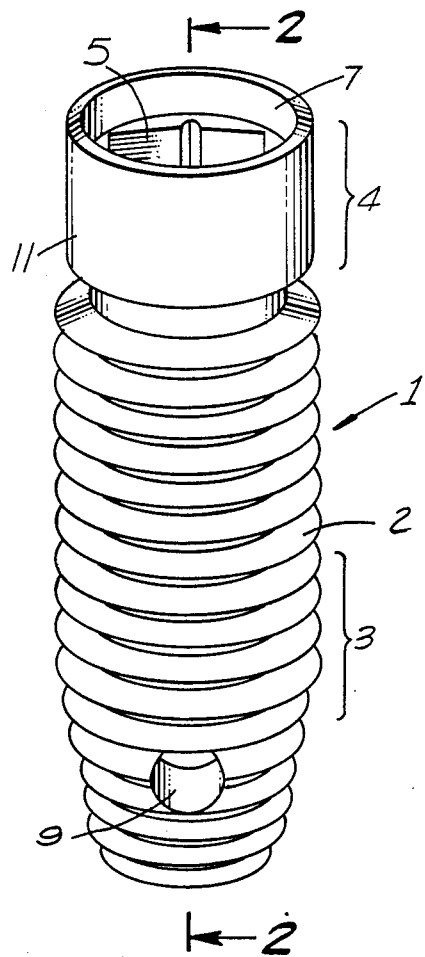
FIG. 1 is a perspective view of one embodiment of the dental implant anchor of this invention.
Figure 2:
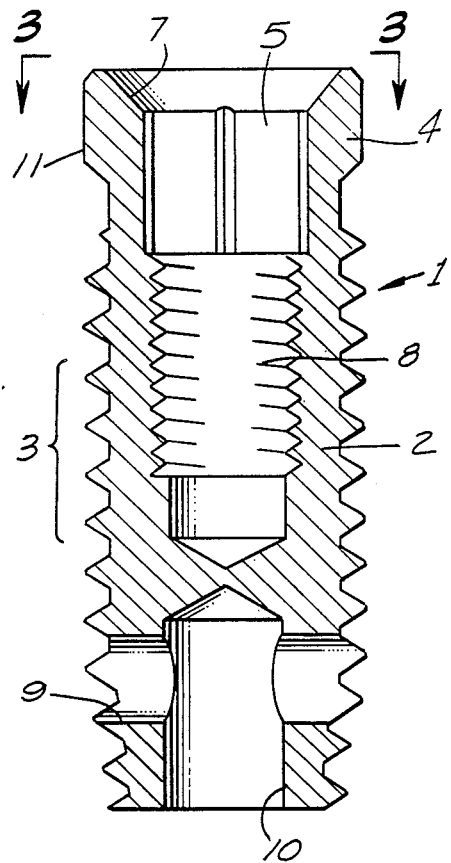
FIG. 2 is a cross-sectional view of the implant embodiment shown in FIG. 1, taken on line 2—2 of FIG. 1.
Figure 3:
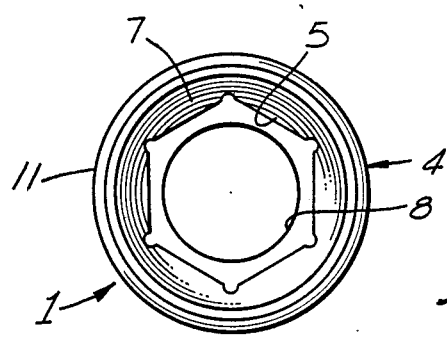
FIG. 3 is a top plan view of the implant embodiment shown in FIGS. 1 and 2.

In embodiment 1 of FIG. 1, body portion 2 of implant 1 has a self-tapping, threaded exterior surface 3. Threaded exterior surface 3 of implant 1 is linked, at the top, to head portion 4. Head portion 4 has a smooth cylindrical-shaped external surface 11 and a hex-shaped internal wall surface 5 for engagement with a wrench such as an Allen-type wrench. Above the hex-shaped internal wall surface is chamfered interior wall surface 7 of head portion 4. Head portion 4 extends a linear distance of about 2 mm inside of implant 1.

Inside body portion 2 of implant 1 is internally-threaded passage 8, which extends from a plane at the base of head portion 4 in parallel to the axis of body portion 2 a linear distance of about 3 mm inside body portion 2.

At the end of implant 1 opposite head portion 4 is opening 9, which extends transversely through, and across the axis of body portion 2. Opening 9 permits the growth of anchoring bone through the opening, after anchoring means 1 has been screwed into the jaw of a subject.

At the end of implant 1, opposite head portion 4, is axial opening 10, which is unthreaded, and which extends a linear distance of about 2 mm into body portion 2.

Internally-threaded passage 8 inside implant 1 can receive a variety of cementable and threaded adaptors already in use, such as threaded copings, threaded screws, and cementable dental prostheses. See, for example, the Core-Vent Corporation publication entitled, "Implant Prosthodontics: An Idea Whose Time Has Come!", published in January, 1986, pp. 6–7.

Figure 4:
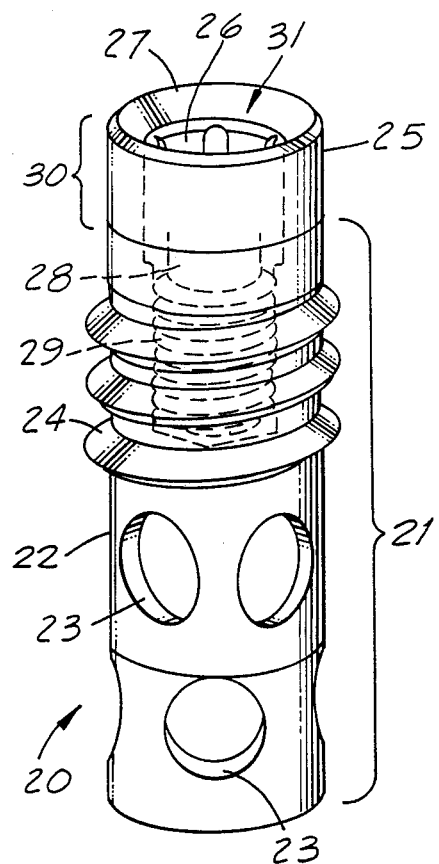
FIG. 4 is a perspective view of another dental implant anchor embodiment that includes internal means for engaging means for inserting the implant into bone tissue.

FIG. 4 shows another dental implant anchoring means 20 having a body portion 21 and a head portion 30. Body portion 21 includes a hollow, vented portion 22 that includes a plurality of vents such as vent 23 and, atop vented portion 22, a threaded portion 24. The implant has an internal shaft 28 extending downwardly and inwardly from opening 31. Shaft 28 has threads 29 on its internal wall below the head portion 30. Head portion 30 has a smooth exterior wall 25, a chamfered surface 27 at its opening 31, and a wrench-engaging surface 26 inside head portion 30. Chamfered surface 27 is adapted to receive, and fit smoothly with inserts adapted to engage and support a dental prosthesis such as a prosthetic tooth.

Figure 5:
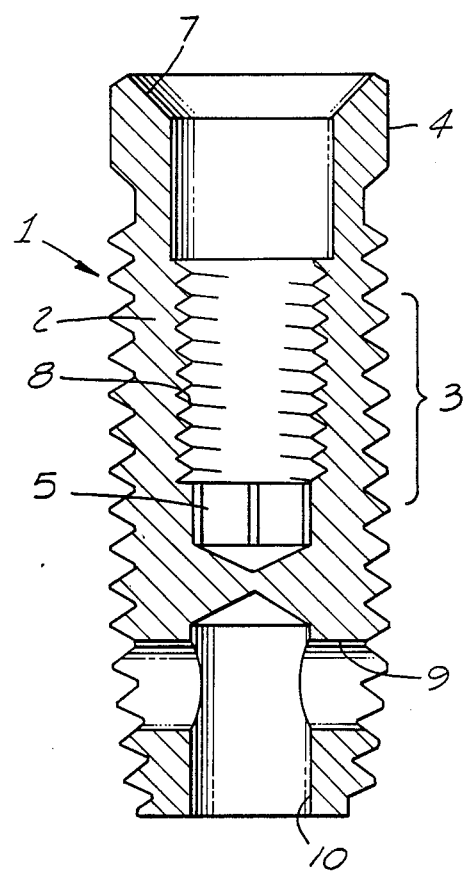
FIG. 5 shows an elevational view, in cross-section, of another dental implant anchor embodiment.

FIG. 5 shows another embodiment of a new dental implant anchoring means of the invention. In most respects, this implant is identical to the implant shown in FIG. 1, except that the internal wrench-engaging surface 5 lies at the bottom of the internal passage inside the implant instead of on the internal surfaces of the top portion of the implant. While FIG. 5 shows the internal passage, below the top portion, to be partially threaded to receive and engage with threaded inserts such as dental prostheses, the threading is not mandatory, and the walls of the internal passage can, in alternative embodiments, be smooth instead of threaded, or partially threaded and partially smooth.

The screw-type dental implant anchoring means of this invention can be inserted into the bone of a subject by a simplified surgical procedure utilizing a pilot drill and two internally-irrigated, end-cutting drills of progressively increasing diameter. Because of effective cooling through the shaft of the burr, it is unnecessary to use all three instruments where porous bone exists, such as in the maxilla. In some embodiments of the new anchoring means, an additional thread at the apex of the anchoring means makes the anchoring means self-tapping.

Alternatively, and particularly where the bone that is intended to receive the anchoring means is dense, the anchoring means can be seated following the creation of threads in the bone of a subject using a titanium bone tap device. Properly inserted in the bone of a subject, the anchoring means of this invention immediately seals the opening through the cortical bone, simplifies the uncovering procedure, and provides a smooth, easily-cleaned supracortical connection to a matching, chamfered edge on a threaded insert.

What is claimed is:

1. A screw-type dental implant anchoring means comprises an externally-threaded body portion joined to a top portion having an unthreaded exterior wall, said implant having an internal, wrench-engaging surface, and an internally-threaded shaft extending downwardly from said top portion into said body portion, said top portion having an outer circumference substantially no greater than the circumference of the externally-threaded body portion, said internal, wrench-engaging surface lying substantially entirely within said shaft, inside said body portion, substantially entirely within the exterior walls of said anchoring means, and substantially entirely below the upper surface of said anchoring means.

2. The dental implant anchoring means of claim 1 further comprising, within said top portion, a chamfered internal surface at the upper opening of said top portion.

3. The dental implant anchoring means of claim 1 wherein said top portion includes, near the opening is in said top portion, a chamfered interior wall surface adapted to receive, engage and support said connectable prosthetic means.

4. The dental implant anchoring means of claim 1 wherein said internally-threaded shaft is above said internal, wrench-engaging surface.

5. The dental implant anchoring means of claim 1 wherein said internally-threaded shaft is below said internal, wrench-engaging surface.

6. The dental implant anchoring means of claim 1 wherein said internally-threaded shaft and said internal, wrench-engaging surface are adapted to receive and engage an adaptor selected from the group consisting of cementable adaptors and threaded adaptors.

7. A dental implant anchoring means comprising an externally-threaded body portion, and an internally-threaded shaft extending longitudinally into said body portion, said implant having internal, wrench-engaging implant insertion means lying substantially entirely within said shaft, substantially entirely inside said body portion, and substantially entirely below the upper surface of said anchoring means.

8. The dental implant anchoring means of claim 7 further comprising, near the top of said shaft, a chamfered interior wall surface adapted to receive, engage and support said connectable prosthetic means.

9. The dental implant anchoring means of claim 7 wherein said internally-threaded shaft is above said internal, wrench-engaging surface.

10. The dental implant anchoring means of claim 7 wherein said internally-threaded shaft is below said internal, wrench-engaging surface.

11. The dental implant anchoring means of claim 7 wherein said internally-threaded shaft and said internal, wrench-engaging surface are adapted to receive and engage an adaptor selected from the group consisting of cementable adaptors and threaded adaptors.

12. A dental implant anchoring means comprising a body portion having threads on part of the external wall surface of the body portion, an internally-threaded shaft extending longitudinally into said body portion, a vent means on another, hollow part of the external wall surface of the body portion, and internal, wrench-engaging means lying substantially entirely inside said shaft, substantially entirely within the exterior walls of said anchoring means, and substantially entirely below the top surface of said anchoring means, for inserting said implant into an opening formed in the tissue.

13. The dental implant anchoring means of claim 12 further comprising a top portion joined to said body portion, said top portion having a smooth external wall.

14. The dental implant anchoring means of claim 12 further comprising a top portion joined to said body portion, said top portion having a smooth external wall.

15. The dental implant anchoring means of claim 12 wherein said internally-threaded shaft is above said internal means.

16. The dental implant anchoring means of claim 12 wherein said internally-threaded shaft is below said internal means.

17. The dental implant anchoring means of claim 16 further comprising a chamfered internal surface of the upper opening of said shaft.

18. The dental implant anchoring means of claim 12 wherein said internally-threaded shaft and said internal, wrench-engaging surface are adapted to receive and engage an adaptor selected from the group consisting of cementable adaptors and threaded adaptors.

19. A screw-type dental implant anchoring means comprising an externally-threaded body portion joined to a top portion having an unthreaded exterior wall, and an internally-threaded shaft inside said body portion, said implant having an internal, wrench-engaging surface lying substantially entirely inside said shaft, substantially entirely within the exterior walls of said anchoring means, substantially entirely below the upper surface of said anchoring means, and inside said body portion for engaging implant insertion wrench means, said top portion being adapted to receive prosthetic connecting means for insertion into the upper surface of said implant anchoring means that forms a smooth, easily cleaned margin with said anchoring means upon insertion into said upper surface.

20. The dental implant anchoring means of claim 19 wherein said threaded shaft extends downwardly from a plane just below said top portion a substantial distance inside the body portion.

21. The dental implant anchoring means of claim 20 further comprising, at the distal end of said anchoring means, a through hole extending from one side of the body portion to the other, and an opening at the bottom of the body portion extending axially upwardly inside the body portion.

22. The dental implant anchoring means of claim 19 further comprising, within said top portion, means for joining said anchoring means to said connecting prosthetic devices.

23. The dental implant anchoring means of claim 19 wherein said internally-threaded shaft extends from a plane just below said top portion downwardly a substantial distance inside said shaft.

24. The dental implant anchoring means of claim 19 wherein said internally-threaded shaft and said internal, wrench-engaging surface are adapted to receive and engage an adaptor selected from the group consisting of cementable adaptors and threaded adaptors.

25. A dental implant anchoring means comprising an externally-threaded body portion, and and internally threaded shift inside said body portion, said implant having internal, wrench-engaging means lying substantially entirely inside said shaft, substantially entirely within the exterior walls of said anchoring means, substantially entirely below the top surface of said anchoring means and inside said body portion for engaging implant insertion wrench means, said anchoring means being adapted to receive prosthetic connecting means that includes post means that fit into said internally-threaded shaft and that form a smooth, easily cleaned margin with said anchoring means upon said insertion into said upper surface.

26. The dental implant anchoring means of claim 25 wherein said internally-threaded shaft is above said internal, wrench-engaging surface.

27. The dental implant anchoring means of claim 25 wherein said internally-threaded shaft is below said internal, wrench-engaging surface.

28. The dental implant anchoring means of claim 25 wherein said internally-threaded shaft and said internal, wrench-engaging surface are adapted to receive and engage an adaptor selected from the group consisting of cementable adaptors and threaded adaptors.

29. A dental implant anchoring means comprising an externally-threaded body portion joined to a top portion having an unthreaded exterior wall, and an internally-threaded shaft inside said body portion, said implant having internal, wrench-engaging means lying substantially entirely inside said shaft, substantially entirely within the exterior walls of said anchoring means, substantially entirely below the top surface of said anchoring means and inside said body portion for engaging implant insertion wrench means, said top portion being adapted to receive prosthetic connecting means that forms a smooth, easily cleaned margin with said anchoring means upon insertion into said upper surface.

30. The dental implant anchoring means of claim 29 wherein said top portion includes, near the opening in said top portion, a chamfered interior wall surface adapted to receive, engage and support said connectable prosthetic means.

31. The dental implant anchoring means of claim 29 wherein said internally-threaded shaft is above said internal, wrench-engaging surface.

32. The dental implant anchoring means of claim 29 wherein said internally-threaded shaft is below said internal, wrench-engaging surface.

33. The dental implant anchoring means of claim 29 wherein said internally-threaded shaft and said internal, wrench-engaging surface are adapted to receive and engage an adaptor selected from the group consisting of cementable adaptors and threaded adaptors.

34. A dental implant anchoring means comprising a top portion joined to a body portion, said body portion having threads on part of the external wall surface of the body portion, a vent means on another, hollow part of the external wall surface of the body portion, and an internally-threaded shaft inside said body portion, and internal, wrench-engaging means lying substantially entirely inside said shaft, substantially entirely within the exterior walls of said anchoring means, substantially entirely below the top surface of said anchoring means, and inside said body portion for engaging wrench means for inserting said implant into an opening formed in jawbone tissue, said top portion being adapted to receive prosthetic connecting means, said prosthetic connecting means when placed in said internally-threaded shaft forming a smooth, easily cleaned margin with said anchoring means upon insertion into said upper surface.

35. The dental implant anchoring means of claim 34 wherein said internally-threaded shaft and said internal, wrench-engaging surface are adapted to receive and engage an adaptor selected from the group consisting of cementable adaptors and threaded adaptors.

36. A dental implant anchoring means comprising a body portion, an internally-threaded shaft extending downwardly from the top of said dental implant anchoring means into said body portion, and an internal, wrench-engaging surface lying substantially entirely within said shaft, substantially entirely within the exterior walls of said anchoring means , and substantially entirely below the top surface of said anchoring means.

37. The dental implant anchoring means of claim 36 further comprising, at the distal end of said anchoring means, a through-hole extending from one side of the body portion to the other, and an opening at the bottom of the body portion extending axially upwardly inside the body portion.

38. The dental implant anchoring means of claim 37 wherein the internal, wrench-engaging surface is adapted to receive a hex wrench.

39. The dental implant anchoring means of claim 36 further comprising a vent means on another, hollow part of the external wall surface of the body portion.

40. The dental implant anchoring means of claim 36 wherein said internally-threaded shaft and said internal, wrench-engaging surface are adapted to receive and engage an adaptor selected from the group consisting of cementable adaptors and threaded adaptors.

41. A dental implant anchoring means comprising an externally-threaded body portion, and an internally-threaded shaft extending downwardly from the top of said implant anchoring means inside said body portion, said implant having an internal, wrench-engaging surface lying substantially entirely inside said shaft, substantially entirely within the exterior walls of said anchoring means, and lying substantially entirely below the top surface of said anchoring means, said shaft being adapted to receive prosthetic connecting means that forms a smooth, easily-cleaned margin with said anchoring means upon insertion into said shaft, said shaft including near the opening at the top of said shaft, a chamfered interior wall surface adapted to receive, engage and support said prosthetic connecting means.

42. The dental implant according means of claim 41 wherein said internally-threaded shaft and said internal, wrench-engaging surface are adapted to receive and engage an adaptor selected from the group consisting of cementable adaptors and threaded adaptors.

43. A dental implant anchoring means comprising a body portion, and an internally-threaded shaft extending downwardly from the top of said implant anchoring means inside said body portion, said implant having an internal, wrench-engaging surface lying substantially entirely inside said shaft, substantially entirely within the exterior walls of said anchoring means, and substantially entirely below the top surface of said anchoring means, said shaft being adapted to receive prosthetic connecting means that forms a smooth, easily-cleaned margin with said anchoring means upon insertion into said shaft, said shaft including near the opening at the top of said shaft, a chamfered interior wall surface adapted to receive, engage and support said prosthetic connecting means.

44. The dental implant anchoring means of claim 43 wherein said internally-threaded shaft and said internal, wrench-engaging surface are adapted to receive and engage an adaptor selected from the group consisting of cementable adaptors and threaded adaptors.

* * * * *

REEXAMINATION CERTIFICATE (3487th)

United States Patent [19]

Niznick

[11] B1 4,960,381

[45] Certificate Issued Apr. 14, 1998

[54] SCREW-TYPE DENTAL IMPLANT ANCHOR

[75] Inventor: Gerald A. Niznick, Encino, Calif.

[73] Assignee: Core-Vent Corporation, Encino, Calif.

Reexamination Request:
No. 90/004,452, Nov. 13, 1996

Reexamination Certificate for:
Patent No.: 4,960,381
Issued: Oct. 2, 1990
Appl. No.: 231,653
Filed: Aug. 10, 1988

Related U.S. Application Data

[63] Continuation of Ser. No. 1,564, Jan. 8, 1987, abandoned.

[51] Int. Cl.$^6$ .......................................... A61C 8/00
[52] U.S. Cl. .............................. 433/174; 433/173
[58] Field of Search .............................. 433/173, 174, 433/175, 176

[56] References Cited

U.S. PATENT DOCUMENTS

| | | | |
|---|---|---|---|
| 4,051,559 | 10/1977 | Pifferi | 3/1.912 |
| 4,324,550 | 4/1982 | Reuther | 433/174 |
| 4,431,416 | 2/1984 | Niznick | 433/174 |
| 4,624,673 | 11/1986 | Meyer | 623/16 |
| 4,713,003 | 12/1987 | Symington | 433/173 |
| 4,713,004 | 12/1987 | Linkow | 433/174 |
| 4,744,754 | 5/1988 | Ross | 433/173 |
| 4,772,204 | 9/1988 | Söderberg | 433/174 |
| 4,826,434 | 5/1989 | Krueger | 433/174 |

FOREIGN PATENT DOCUMENTS

| | | |
|---|---|---|
| 0000549 | 2/1979 | European Pat. Off. . |
| 540713 | 3/1956 | Italy . |
| 413224 | 12/1966 | Switzerland . |
| 1291470 | 10/1972 | United Kingdom . |
| WO8302555 | 8/1993 | WIPO . |

*Primary Examiner*—Cary F. O'Connor

[57] ABSTRACT

A screw-type dental implant anchor includes an externally-threaded body portion having internal structure for engaging an insertion tool. The body portion can be joined to a top portion having an unthreaded exterior wall. This internal is inside a top portion or inside the body portion of the anchor. The top portion is open, preferably chamfered at its upper end, and in registration with an internally-threaded shaft inside the body portion of the anchor that extends from a plane just below the head portion downwardly a substantial distance inside the body portion. The distal end of the anchor includes a through hole extending from one side of the body portion to the other, and an opening at the bottom of the body portion extending upwardly inside the body portion a distance sufficient to permit bone and associated tissue to grow into and through these openings and to permit blood tissue to escape.

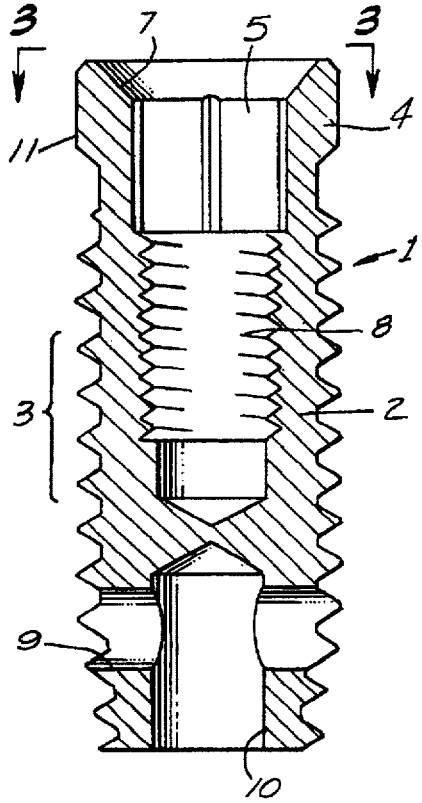

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–35, 41–43 and 44 is confirmed.

Claims 36 and 38 are determined to be patentable as amended.

Claims 37, 39 and 40, dependent on an amended claim, are determined to be patentable.

New claims 45–47 are added and determined to be patentable.

36. A dental implant anchoring means comprising a body portion, an internally-threaded shaft extending downwardly from the top of said dental implant anchoring means into said body portion, *said internally-threaded shaft terminating inside said body portion,* and an internal, wrench-engaging surface lying substantially entirely within said shaft, substantially entirely within the exterior walls of said anchoring means, and substantially entirely below the top surface of said anchoring means.

38. [The dental implant anchoring means of claim 37] *A dental implant anchoring means comprising a body portion, an internally-threaded shaft extending downwardly from the top of said dental implant anchoring means into said body portion, and an internal, wrench-engaging surface lying substantially entirely within said shaft, substantially entirely within the exterior walls of said anchoring means, and substantially entirely below the top surface of said anchoring means,* wherein the internal, wrench-engaging suface [is] adapted to receive a hex wrench.

*45. The dental implant anchoring means of claim 36 wherein said body portion and said internally-threaded shaft are cylindrically-shaped over substantially their entire length.*

*46. The dental implant anchoring means of claim 36 wherein said internal, wrench-engaging surface is multi-sided, and includes at least six sides.*

*47. The dental implant anchoring means of claim 46 wherein said internal wrench-engaging surface and said internally-threaded shaft are together adapted to receive and engage a multi-sided adaptor.*

* * * * *